United States Patent [19]
Golovistikov et al.

[11] Patent Number: 6,150,326
[45] Date of Patent: *Nov. 21, 2000

[54] MEANS FOR TREATING AUTOIMMUNE DISEASES AND METHOD FOR THE TREATMENT THEREOF

[75] Inventors: Ivan Nikolaevich Golovistikov, Donbasskaya str, 5, ap. 51, Moscow, Russian Federation; Leonid Yazonovich Kacharava, Mirtskhulava str, 2, ap. 45, Tbilici, Georgia; Jury Semyonovich Tatarinov; Khallar Abdumuslimovich Alikhanov, both of Moscow, Russian Federation

[73] Assignees: Leonid Yazonovich Kacharava, Tbilici, Georgia; Ivan Nikolaevich Golovistikov, Moscow, Russian Federation

[ * ] Notice: This patent issued on a continued prosecution application filed under 37 CFR 1.53(d), and is subject to the twenty year patent term provisions of 35 U.S.C. 154(a)(2).

[21] Appl. No.: 08/716,139

[22] PCT Filed: Mar. 16, 1995

[86] PCT No.: PCT/RU95/00047

§ 371 Date: Nov. 15, 1996

§ 102(e) Date: Nov. 15, 1996

[87] PCT Pub. No.: WO95/25531

PCT Pub. Date: Sep. 28, 1995

[30] Foreign Application Priority Data

Mar. 18, 1994 [RU] Russian Federation ............. 94008169

[51] Int. Cl.$^7$ ................................................ A61K 38/16
[52] U.S. Cl. ............................ 514/8; 530/395; 530/397; 436/63
[58] Field of Search ................................ 514/8; 530/395, 530/397; 436/63

[56] References Cited

U.S. PATENT DOCUMENTS

| | | | |
|---|---|---|---|
| 4,275,000 | 6/1981 | Ross | 260/112 |
| 5,118,669 | 6/1992 | Noguchi et al. | 514/17 |
| 5,169,835 | 12/1992 | Chan | 514/8 |
| 5,559,097 | 9/1996 | Sasser | 514/21 |

FOREIGN PATENT DOCUMENTS

| | | |
|---|---|---|
| 2650183 | 2/1991 | France . |
| 1061818 | 12/1983 | Russian Federation . |
| 1657190 | 6/1991 | Russian Federation . |
| 676467 | 4/1987 | Switzerland . |
| 2170707 | 8/1986 | United Kingdom . |
| 2251186 | 7/1992 | United Kingdom . |
| 8801875 | 3/1988 | WIPO . |
| 8805297 | 7/1988 | WIPO . |
| 9110443 | 7/1991 | WIPO . |

OTHER PUBLICATIONS

Gorlina et al, The Soviet Journal of Developmental Biology (English translation of Ontogenez) 14 (6):366–369, Sept. 1984.

Effect on Pregnancy and Hormonal Changes on the Activity of Rheumatoid Arthritis Monika Ostensen, et al, Dept. of Rheumatology, Institute of Clinical Medicine, Univ. of Tromso, Norway, Scand J. Rheum. 12:69–72, 1983.

Suppressor Cell Activity After Concanavalin a Treatment of Lymphocytes from Normal Donors, Shou, et al, Journal of Experimental Medicine vol. 143, 1100–1110; 1976.

Inhibitory and Stimulatory Effects of Concanavalin on the Response of Mouse Spleen Cell Suspensions to Antigen, Richard Dutton, Journal of Experimental. Medicine vol. 138, pp. 1496–1505 (1973).

Immunochemical Identification of New Beta–1–Globulin in the Blood Serum of Pregnant Women, Bulletin of Experimental Biology and Medicine, 1970 No. 6, Medicina Publishers, Moscow, pp. 66–68, Figs. 1–2.

Human Trophoblastic Beta–1–Globulin and Chorionepithelioma, Tatarinov, et al, Onco Developmental Gene Expression, 1976, pp. 463–468.

*Primary Examiner*—Lorraine Spector
*Assistant Examiner*—Eliane Lazar-Wesley
*Attorney, Agent, or Firm*—Ladas & Parry

[57] ABSTRACT

Trophoblastic β-I-glycoprotein (TBG) is used as a means for treating autoimmune diseases showing suppressors immunodeficit.

A method of treating of autoimmune diseases comprises the administration of an immune correcting preparation, said preparation being trophoblastic β-I-glycoprotein (TBG), indications with respect to said preparation being determined by testing TBG sensitivity of mononuclear cells (MNCs).

12 Claims, 1 Drawing Sheet

MEANS FOR TREATING AUTOIMMUNE DISEASES AND METHOD FOR THE TREATMENT THEREOF

FIELD OF TECHNOLOGY

The present invention relates to medicine, more specifically to the use of immune correcting preparations for the treatment of autoimmune diseases.

The present invention can be used as a medication for diagnosing a suppressor component of human immune status and for evaluating the possibility of treating autoimiune diseases, in particular, disseminated sclerosis, rheumatic arthritis, etc.

PRIOR ART

Known is β-I-qlycoprotein of placental origin which is a of trophoblastic β-I-glycoprotein (TBG), used as a growth and proliferation stimulator for hematopoietic blood cells (U.S. Pat. No. 5,169,835, cl. A61K 35/50, 1989).

Nevertheless the known compound has not been used as a means for treating of autoimmune diseases.

Known is the use of TBG for diagnosing and prognosticating the course of pregnancy (see L.G. Sotnikova, I.N. Golovistikov et al., *The Role of β-I-glycoprotein Trophoblast in Diagnosing and Prognosticating Pregnancy*, Metodicheskije Recomendatsii, Moscow, 1984).

Nevertheless said work does not disclose the possibility of using TBG for diagnosing a suppressor component and treating autoimmune diseases.

Known is the method for treating pustular psoriasis by administering a drug of placental origin (see the USSR Inventor's Certificate No.106181, cl. A61K 35/50 as of Jul. 19, 1982)

Nevertheless the use of the drug according to said method fails to prevent side effects which may occur due to impurities.

Known is the method for treating autoimmune diseases comprising administering of a dosage of an immune correcting preparation of placental origin (see the USSR Inventor's Certificate No. 1657190, cl. A61K 35/50 as of 1989).

Nevertheless said method employs a preparation containing impurities which may cause allergic reactions, moreover said preparation is effective only during postsurgical period and is limited to autoimmune orchitis.

SUMMARY OF THE INVENTION

The main object of the present invention is to provide an effective method of treatment of autoimmune diseases by administering a preparation which shows an immune correcting activity and does not cause side effects, as well as to broaden the range of autoimmune diseases which can be treated therewith.

Said object is achieved by new use of trophoblastic β-I-glycoprotein (TBG) as a means for treating autoimmune diseases, and the method of treatment of autoimmune diseases comprising the administration of the immune correcting preparation according to the invention, additionally comprises a prestudy of immune status, and in case a deficit of suppressors is determined, then trophoblastic β-I-glycoprotein (TBG) is used as an immune correcting preparation.

The prestudy of immune status may comprise collecting a sample of peripheral blood, obtaining mononuclear cells (MNCs), dividing the sample into two portions, cultivating the first portion without TBG, and cultivating the second one with TBG, washing MNCs out of culture medium, blocking proliferation, adding into each of said MNC portions newly isolated MNCs obtained from a normal donor, which latter MNCs having been stimulated with phytohemagglutinin in equal proportions to produce test cultures, cultivating said cultures, further evaluating the proliferation of said cultures and determining the suppression values based on the ratios of the levels of proliferation in test cultures.

Experiments and clinical tests have shown new properties of TBG as an immune correcting preparation useful for treating different autoimmune diseases.

The study of immune status values for 154 patients suffering autoimmune diseases (disseminated sclerosis, rheumatic arthritis, etc.) has shown T-suppressors deficit, which is starting mechanism for autoimmunization, i.e. for the loss of autotolerance.

The treating effect of TBG based on its ability to induce suppressive activity of lymphocytes in patients suffering disseminated sclerosis, rheumatic arthritis, etc.

Clinical immunological surveys carried out on the patients suffering abovementioned diseases and on a control group (105 donors) comprised the evaluation of the functional activity of T-suppressors. Mononuclear cells (MNCs) were isolated from peripheral blood by centrifuging in phycollurotrust single-stage density gradient (Boyum,1968).

It has been stated that in patients suffering the disseminated sclerosis the relative number of T-cells during acute stage of the disease (41.3±2%) was below the normal value (63.2±2%) by the factor of 1.5.

Based on the preliminary test data one can make the conclusion that TBG can be used for treating all patients suffering acute stage of the disease, 40% of patients being in remission, and with respect to the rest 60% of patients the administration of TBG should be temporarily avoided.

The preparation for administration may be prepared in the form of an injectable solution as a combination with any pharmaceutically acceptable solvent.

The dosages and administration methods depend on the nature and stage of the disease. The dosage range for TBG may be from 3 to 120 μg/ml of patient's blood.

TBG is highly effective and a marked result is achieved even with a one time administration of a minimum dose.

Preferably TBG should be administered parenterally or intravenously after preculturing TBG in the concentration of 60 μg/ml with auto-MNC from peripheral blood.

BRIEF DESCRIPTION OF THE DRAWING

Further details of the present invention are disclosed in the examples of specific embodiments as well as in the drawing wherein.

PREFERRED EMBODIMENT OF THE INVENTION

Figure 1:
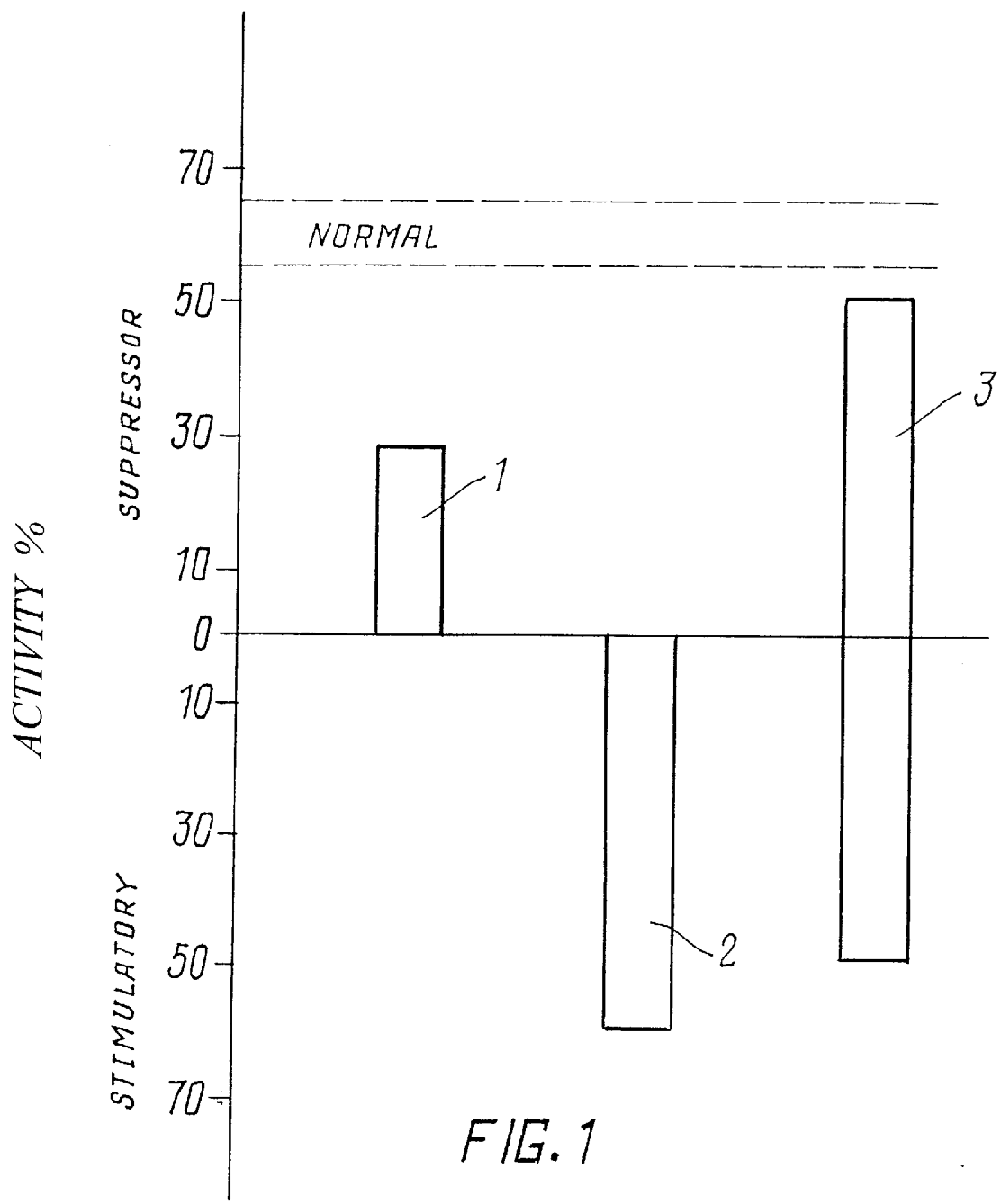
FIG. 1 discloses stipulatory (countersuppressor) and suppressor activity as percentage of TBG-induced lymphocytes in peripheral blood of the patients suffering disseminated sclerosis at the acute stage (1), at the initial stage of remission (2), and at the remission stage (3).

The prestudy of the immune status is carried out by testing TBG sensitivity of mononuclear cells (MNC) in the following steps.

The peripheral blood is taken from a patient using venipuncture, placed into tubes with heparin solution, then a suspension of mononuclear cells (MNCs) is obtained by cells sedimentation in phycoll-urotrust single-step gradient, and divided into two portions. The first portion is cultivated during 48 hours without suppressor activator (TBG), and the second one is cultivated with TBG. Further MNCs are washed out of the culture medium and the proliferation is blocked by treating MNC with mitomycin C.

At the next step newly isolated lymphocytes from a normal donor (which lymphocytes have been stimulated with phytohemagglutinin (PHA) in order to be used as responding test cells) are added into each of the above mentioned portions of control and TBG-stimulated lymphocytes in equal proportions to obtain test cultures. Cultivation is carried out for 72 hours. Then the proliferation of test cultures is evaluated using H3-thymidine, and the suppression is evaluated by degree of proliferation decrease therein.

Suppression index (SI) is determined using the following formula:

$$SI = \left(1 - \frac{\text{pulse number/min. in test culture with } TBG}{\text{pulse number/min. in test culture without } TBG}\right) \times 100\%$$

Suppression index characterizes the suppressor component of human inmmune status. Depending on the data obtained as a result of studying patient's immune status further methods of treatment of the autoimmune disease are determined.

The present invention is further illustrated by the following examples.

EXAMPLE 1

Patient C., 29. Diagnosis: disseminated sclerosis (cerebromedullary form, prolonged remissions); the patient has received several treatments with corticosteroid preparations; the immunological study carried out during the remission stage snowed that stimulatory (countersuppressor) activity T-lymphocytes in peripheral blood was 28%. At the present stage the treatment with TBG should be avoided.

EXAMPLE 2

Patient B., 28, diagnosis: disseminated sclerosis (cerebromedullary form, remittent course, acute stage). Duration: 3 years. Neurological status: lateral nistagmus when looked right; vivid tendon reflexes; feet: D>S. Abdominal reflexes: upper low, medium and lower reflexes are not presented. Two-side toe (Babinsky's) symptom. Foot clonus is more rough to the right. No paresis of members, unchanged tonus are determined. Atactic walking. Unstable in Romberg position. Ataxia during knee-heel test, delayed urination.

Spinal liquor:

Protein—0.76%,

Lange reaction—66644322.

Oculist's inspection: pale temple sections of the discs.

T-suppressor activity in peripheral blood during TBG induction—17%.

Under aseptic conditions one 110 ml blood sample was taken from the patients arm vein. Mononuclear cells (MNCS) had been isolated according to the standard method in the density gradient of phycoll-urotrust. Isolated MNCs were cultivated with TBG in the concentration of 60 μg/ml. After having been washed by centrifuging the cells were introduced intravenously. The signs of remission were observed on the 5th day. The walking and urination became normal. Stability in Romberg position was acquired. Kneel-heel test was performed clearly. Restudy of immune status showed increase in the functional activity of T-suppressors in peripheral blood with TBG induction of 38%. Ouhterloni tests performed on the 7th, 14th and 28th days had not determined anti-TBG antibodies in the patient.

EXAMPLE 3

Patient H., 42, came to the hospital with the diagnosis of rheumatoid arthritis (polyarthritis, seropositive, A—P (stage 2) insufficient joints functioning (IJF). T-suppressor activity of peripheral blood under TBG induction was 22%.

The patient received TBG injections into the joints suffering pathological changes, each injection of 0.5 ml having the concentration of 60 μg/ml. Remission was observed on the fourth day. Pain syndrome weakened. Insufficient joints functioning regressed. Restudy showed 47% increase in T-suppressors functional activity in periphedral blood under TBG induction. Ouhterloni tests performed on the 7th, 14th and 28th days had not determined anti-TBG antibodies in the patient.

The study of 105 donors and 154 patients suffering different autoimmune diseases showed that the use of TBG in the dosage less than 3 μg/ml of blood produced insufficient effect, while the use of the dosages over 120 μg/ml of blood was undesirable.

The normal value of suppressors activity is 63.4%±4.7, at the acute stage this value is 20.5%±9.8, during remission it is 47.7%±2.8, at the initial stage of remission said value is 66.6%±16.1 (stimulatory activity).

Therefore TBG preparation has shown a high activity as a means for treating autoiminune diseases. The method of treating autoimmune diseases according to the present invention provides an effective treatment of different autoimmune diseases without causing undesirable side effects.

INDUSTRIAL APPLICABILITY

The present invention can be widely used as a means for treating a broad range of autoimmune diseases as well as for diagnosing the suppressor component of human immune status.

What is claimed is:

1. A method for treating a patient having an autoimmune disease, said method comprising the steps of: (a) testing the patient to determine if the patient has a deficit of lymphocyte suppressor activity; and (b) if and only if the deficit of suppressor activity is detected in step (a), administering to the patient trophoblastic β-I-glycoprotein (TBG) in an amount effective to increase the lymphocyte suppressor activity in the patient.

2. A method for treating a patient as claimed in claim 1, wherein the TBG is administered to the patient in dosage of from about 3 to 120 mcg per ml of blood of the patient.

3. A method for treating a patient as claimed in claim 2, wherein the TBG is administered parenterally.

4. A method for treating a patient as claimed in claim 2, wherein the TBG is incubated with mononuclear cells isolated from peripheral blood of the patient and is administered intravenously with the mononuclear cells.

5. A method for treating a patient as claimed in claim 1, wherein the TBG is administered to the patient during an acute stage of the autoimmune disease.

6. A method for treating a patient as claimed in claim 5, wherein the TBG is administered to the patient in an amount sufficient to increase a suppressor activity of lymphocytes in peripheral blood of the patient by at least about 38% with respect to the lymphocyte suppressor activity in the peripheral blood before administration of the TBG.

7. A method for treating a patient as claimed in claim 1, wherein the testing in step (a) to determine if the patient has the deficit of lymphocyte suppressor activity comprises (a) obtaining first and second portions of blood from the patient and cultivating the first portion with TBG and the second portion without TBG, and (b) determining the lymphocyte suppressor activity by comparing proliferation of responder cells of a test culture in the first portion cultivated with TBG with proliferation of responder cells of the test culture in the second portion cultivated without TBG.

8. A method for treating a patient as claimed in claim 1 wherein the TBG is administered to the patient when a suppressor index of the patient's immune status is 22% or below as determined by (a) obtaining first and second portions of peripheral blood from the patient and cultivating the first portion with TBG and the second portion without TBG, (b) measuring proliferation of responder cells of a test culture in the first portion cultivated with TBG and proliferation of responder cells of the test culture in the second portion cultivated without TBG, and (c) calculating the suppressor index according to the following formula:

proliferation of test culture with TBG suppressor index=(1-proliferation of test culture without TBG)×100%.

9. A method as claimed in claim 1, wherein the testing in step (a) comprises comparing a suppressor activity of the patient with a normal value of suppressor activity and if the suppressor activity is below the normal value, administering the TBG in step (b) in an amount that raises the suppressor activity of the patient toward the normal value.

10. A method as claimed in claim 1, wherein the patient has disseminated sclerosis or rheumatoid arthritis.

11. A method for treating a patient suspected of having a deficit suppressor activity of lymphocytes associated with an autoimmune disease, said method comprising (a) testing the patient to determine if the patient has the deficit of lymphocyte suppressor activity; and (b) if and only if the deficit of suppressor activity is detected in step (a), administering to the patient a composition consisting essentially of trophoblastic $\beta$-I-glycoprotein (TBG) and a pharmaceutically acceptable solvent in an amount effective to increase the lymphocyte suppressor activity in the patient.

12. A method as claimed in claim 11, wherein the testing in step (a) comprises comparing a suppressor activity of the patient with a normal value of suppressor activity and if the suppressor activity is below the normal value, administering the TBG in step (b) in an amount that raises the suppressor activity of the patient toward the normal value.

* * * * *